US00PP16394P3

(12) United States Plant Patent
Murakami

(10) Patent No.: US PP16,394 P3
(45) Date of Patent: Mar. 28, 2006

(54) *NIEREMBERGIA* PLANT NAMED 'SUNNIPARISOBU'

(50) Latin Name: ***Nierembergia* sp.**
Varietal Denomination: Sunniparisobu

(75) Inventor: Yasuyuki Murakami, Gamo-gun (JP)

(73) Assignee: Suntory Flowers Limited, Tokyo (JP)

( * ) Notice: Subject to any disclaimer, the term of this patent is extended or adjusted under 35 U.S.C. 154(b) by 84 days.

(21) Appl. No.: 10/815,188

(22) Filed: Mar. 31, 2004

(65) Prior Publication Data

US 2005/0223453 P1 Oct. 6, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP13,934 P2 7/2003 Murakami

FOREIGN PATENT DOCUMENTS

JP PBR 9448 10/2001

OTHER PUBLICATIONS

Takii's Flowers Guide, Spring in 2004, Takii's & Company, Ldt. (3pp). Published 2002.*
Ramm Botanicals Pty Ltd, AU, "Colour Wave Collection 2003–4 . . . beautiful flowering plants" Published 2002, (with Brief explanation).*
Flower & Green, the newest Catalog 2004, Suntory Flowers, Ltd., (4 pp), Published 2003, with brief English explanation and partial translation of pp. 15 and 16.

The 2004 Suntory Collection, Jackson & Perkins Wholesale, Inc., (3 pp), Published 2003.

Pineae Peak Performers featuring the 2004 Suntory Collection, Pineae Greenhoses, Inc., (4 pp), Published 2003.

Suntory Collection 2004, Moerheim New Plant bv, (3 pp), Published 2003.

Explanation of Publication of Japanese PBR Registration and family documents therein.

Partial English translation of p. 115 of *Takii's Flowers Guide, Spring in 2004*, Takii & Company, Ltd., (3 pp), Published 2002, previously filed Aug. 12, 2004.

* cited by examiner

*Primary Examiner*—Anne Marie Grunberg
*Assistant Examiner*—Annette H Para
(74) *Attorney, Agent, or Firm*—Christie, Parker and Hale, LLP

(57) ABSTRACT

Disclosed herein is a new and distinct variety of *Nierembergia* plant having an erect growth habit. The *Nierembergia* plant has many branches, and a great profusion of blooms, the whole plant remaining in bloom for a considerable period of time. The flowers are single and large, the petals having light purple with strong purple towards the center. Yellow eye presents at the bottom of corolla throat. The plant exhibits high resistance to heat, cold, rain and disease.

2 Drawing Sheets

Botanical/classification: *Nierembergia* sp.
Varietal denomination: Sunniparisobu.

BACKGROUND OF THE VARIETY

The present invention relates to a new and distinct variety of *Nierembergia* plant, which originated from the crossing of *Nierembergia* hybrid varieties 'NB4' as the female parent and 'N10' as the male parent. 'Sunniparisobu' is a vegetative propagated variety.

The female parent 'NB4' (unpatented) used in the crossing to produce 'Sunniparisobu' is a strain of our breeding lines grown at Yokaichi-shi, Shiga-ken, Japan, having a tufted, bushy shape. The plant height is lower than 'Sunniparisobu'. The flowers are single and large, having strong purple petals.

The male parent 'N10' (unpatented) used in the crossing to produce 'Sunniparisobu' is a strain of our breeding lines grown at Yokaichi-shi, Shiga-ken, Japan, having erect growth habit. The plant height is about the same as 'Sunniparisobu'. The flowers are single and medium size, having light purple with strong purple towards the center.

In July 1995, the crossing of 'NB4' as the female parent and 'N10' as the male parent was conducted at Yokaichi-shi, Shiga-ken, Japan, and seedlings were obtained. In October 1996, one seedling was selected in view of its growth habit, flower size and color. That seedling was propagated by cutting, and a trial was carried out by flower potting in the glasshouse and field from May to October 1997, at Yokaichi-shi, Shiga-ken, Japan. The botanical characteristics of that plant were then examined, using similar varieties 'Sunnicobu' (U.S. Plant Pat. No. 13,934) and 'Montebranco' (unpatented) for comparison. As a result, it was concluded that this *Nierembergia* plant is distinguishable from any other variety, whose existence is known to us, and is uniform and stable in its characteristics. The new variety of *Nierembergia* plant was named 'Sunniparisobu'.

In the following description, the color-coding is in accordance with the Colour Chart of The Royal Horticultural Society, London, England (R.H.S.).

SUMMARY OF THE VARIETY

The new variety is unlike any *Nierembergia* commercially available as evidenced by the following unique combinations of characteristics.

1. Erect growth habit with many branches.
2. Great profusion of blooms with the entire plant remaining in bloom for a considerable period of time.
3. The flowers are single and large. The petal color is light purple (near R.H.S. 85B) with strong purple (near R.H.S. 86B) towards the center. Yellow eye presents at the bottom of corolla throat.
4. The plant has a high resistance to rain, cold, heat and disease.

The new variety 'Sunniparisobu' differs from the similar variety 'Sunnicobu' in the following points.

1. The growth habit of 'Sunniparisobu' is erect, while 'Sunnicobu' is tufted.
2. The plant of 'Sunniparisobu' is larger than that of 'Sunnicobu'.
3. The leaf of 'Sunniparisobu' is larger than that of 'Sunnicobu'.
4. The flower diameter of 'Sunniparisobu' is larger than that of 'Sunnicobu'.
5. The rain, heat, disease resistance of 'Sunniparisobu' is stronger than that of 'Sunnicobu'.

The new variety 'Sunniparisobu' differs from the similar variety 'Montebranco' in the following points.

1. The growth habit of 'Sunniparisobu' is erect, while 'Montebranco' is tufted.
2. The plant of 'Sunniparisobu' is larger than that of 'Montebranco'.
3. The leaf of 'Sunniparisobu' is longer than that of 'Montebranco'.
4. The flower diameter of 'Sunniparisobu' is larger than that of 'Montebranco'.
5. The petal color of 'Sunniparisobu' is light purple (near R.H.S. 85B) with strong purple (near R.H.S. 86B) towards the center, while 'Montebranco' is yellowish white (near R.H.S. 155D).
6. The rain, heat, disease resistance and cold hardiness of 'Sunniparisobu' are stronger than those of 'Montebranco'.

This new variety of *Nierembergia* Plant 'Sunniparisobu' was asexually reproduced by the use of cuttings at Yokaichi-shi, Shiga-ken, Japan, and homogeneity and stability thereof were confirmed. The instant plant retains its distinctive characteristics and reproduces true to type in successive generations.

BRIEF DESCRIPTION OF THE PHOTOGRAPH

The depicted plants had been reproduced by the use of cuttings and were photographed during September 1998 while growing outdoor field at an age of approximately 10 months at Yokaichi-shi, Shiga-ken, Japan.

Figure 1:
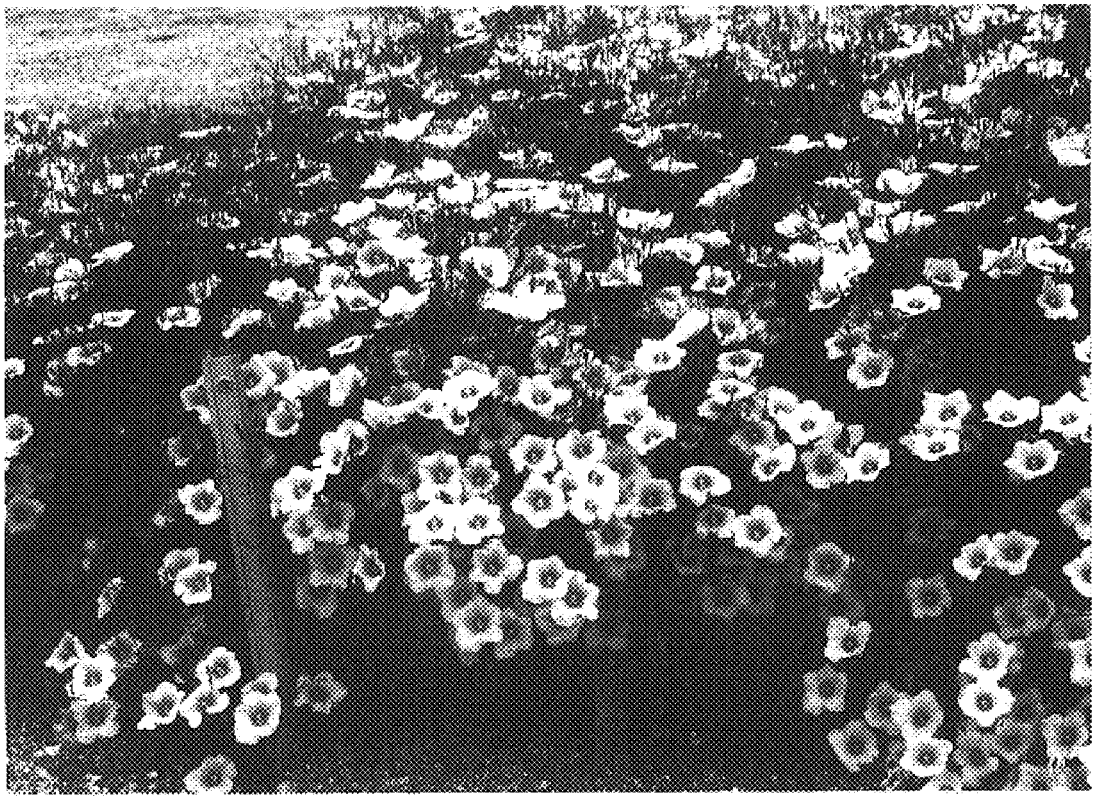
FIG. 1 illustrates a typical plant of the new variety of *Nierembergia* plant 'Sunniparisobu'.
Figure 2:
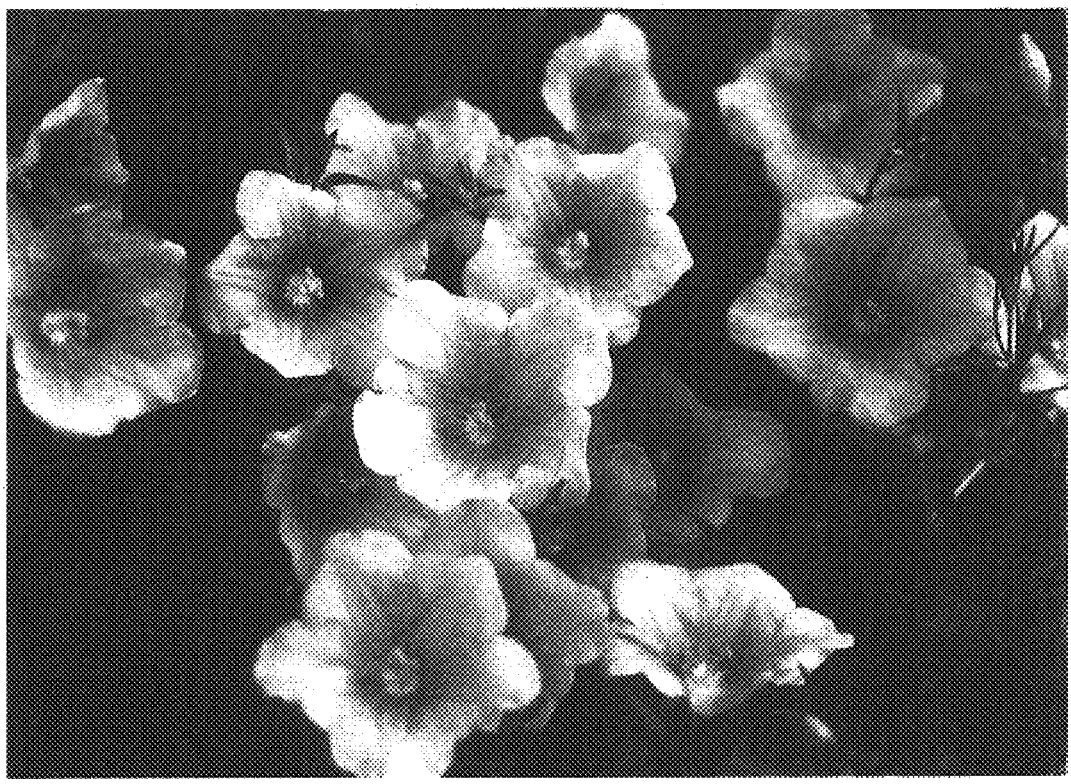
FIG. 2 illustrates flowers of the new variety of *Nierembergia* plant 'Sunniparisobu'.

The botanical characteristics of the new and distinct variety of *Nierembergia* plant named 'Sunniparisobu' are as follows, when observed during September at Yokaichi-shi, Shiga-ken, Japan, at an age of approximately 10 months.

Plant:
- *Growth habit.*—Erect.
- *Height.*—Approximately 32 cm.
- *Spread.*—Approximately 30 cm.

Stem:
- *Thickness.*—Approximately 2.0 mm.
- *Color.*—Near R.H.S. 146A (moderate olive green).
- *Branching.*—Abundant.
- *Pubescence.*—Present.
- *Length of internode.*—Approximately 11 mm.

Leaf:
- *Whole shape.*—Lanceolate.
- *Length.*—Approximately 38 mm.
- *Width.*—Approximately 4.5 mm.
- *Color of upper side.*—Near R.H.S. 146A (moderate olive green).
- *Pubescence.*—Absent.
- *Attachment angle to stem.*—Horizontal.
- *Petiole.*—Absent.

Flower:
- *Facing direction.*—Upward.
- *Type.*—Single.
- *Shape.*—Cup-shaped, with five-fissures.
- *Diameter.*—Approximately 37 mm.
- *Shape of petal tip.*—Obtuse. Considerable variation in the shape and size.
- *Petal margin.*—Entire, occasionally sinuate.
- *Length of corolla tube.*—Approximately 15 mm.
- *Color of petal.*—Upper side: Near R.H.S. 85B (light purple) with near R.H.S. 86B (strong purple) toward the center. Reverse side: Near R.H.S. 91D (very pale purple).
- *Eye color.*—Near R.H.S. 7B (brilliant greenish yellow).
- *Size of eye color.*—Approximately 5.6 mm.
- *Outside color of corolla tube.*—Near R.H.S. 85B (light purple).
- *Flowering habit.*—When planted in April in Japan, the blooming period extends from June to October.

Pistil:
- *Number.*—1.
- *Color of stigma.*—Near R.H.S. 144A (Strong yellow green).

Stamen:
- *Number.*—5.
- *Type.*—Epigynoecious.
- *Color of anther.*—Near R.H.S. 12A (vivid yellow).

Hardiness:
- *Winter.*—USDA Hardiness Zone 8–12 (grown as perennial).
- *Rain.*—No serious damage has been observed during the rainy season (June–July) in Japan. However, heavy rain may damage flower petals due to their thinness, which is a common phenomenon in the *Nierembergia* genus.
- *Heat.*—The plant grows well at temperatures up to at least 35° C.

Resistance:
- *Disease.*—No serious damage by powdery mildew or root rot has been observed.
- *Insect.*—Good. Under the dry condition, may have some damage by the spider mite.

This new variety of *Nierembergia* plant 'Sunniparisobu' is most suitable for flower bedding and potting.

It is claimed:

1. A new and distinct variety of *Nierembergia* plant named 'Sunniparisobu', substantially as herein illustrated and described.

* * * * *